United States Patent [19]

Alfano et al.

[11] Patent Number: 5,293,872
[45] Date of Patent: Mar. 15, 1994

[54] METHOD FOR DISTINGUISHING BETWEEN CALCIFIED ATHEROSCLEROTIC TISSUE AND FIBROUS ATHEROSCLEROTIC TISSUE OR NORMAL CARDIOVASCULAR TISSUE USING RAMAN SPECTROSCOPY

[76] Inventors: Robert R. Alfano, 3777 Independence Ave., Bronx, N.Y. 10463; Cheng H. Liu, 140-25 Ash Ave., Apt. 3A, Flushing, N.Y. 11355

[21] Appl. No.: 678,637

[22] Filed: Apr. 3, 1991

[51] Int. Cl.$^5$ ............................................. A61B 6/00
[52] U.S. Cl. .................................... 128/664; 128/665; 606/7; 606/14; 606/15
[58] Field of Search ............... 128/395, 398, 664, 665; 606/7, 13-16

[56] References Cited

U.S. PATENT DOCUMENTS

| | | |
|---|---|---|
| 4,718,417 | 1/1988 | Kittrell et al. |
| 4,785,806 | 11/1988 | Deckelbaum |
| 4,930,516 | 6/1990 | Alfano et al. |

FOREIGN PATENT DOCUMENTS

| | | |
|---|---|---|
| 2-22331 | 7/1983 | Japan |
| 8902718 | 4/1989 | PCT Int'l Appl. |

OTHER PUBLICATIONS

Patent Abstract No. 117:187825x entitled "Systems and methods of molecular spectroscopy to provide for the diagnosis of tissue".
Nie et al., Spectroscopy, vol. 5, No. 7, pp. 26-31 (1990).
Alfano et al., IEEE J. of Quantum Electronics, vol. QE-23, No. 10, pp. 1806-1811 (1987).
Optics & Photonics, published by the Optical Society of America, vol. 2, No. 2, p. 27 (Feb. 1991).
Redd et al., abstract entitled "Raman Spectroscopy of Atherosclerotic Plaque: Implications for Laser Angioplasty," Radiology, vol. 177, p. 262 (Nov. 1990 Supp.).

*Primary Examiner*—Ruth S. Smith
*Attorney, Agent, or Firm*—Kriegsman & Kriegsman

[57] ABSTRACT

A method for distinguishing between calcified atherosclerotic tissue and either fibrous atherosclerotic tissue or normal cardiovascular tissue. The present method is based on the discovery that, when irradiated with a beam of monochromatic infrared light, calcified atherosclerotic human aortic tissue produces a Fourier Transform Raman spectrum which is distinguishable from analagous spectra obtained from fibrous atherosclerotic human aortic tissue and normal human aortic tissue. Some salient differences in the respective Raman spectra are the presence of five Raman bands at Raman shifts of 957, 1071, 1262-1300, 1445, and 1659 cm$^{-1}$ ($\pm 4$ cm$^{-1}$ for all shifts) for the calcified tissue as compared to three Raman bands at Raman shifts of 1247-1270, 1453 and 1659 cm$^{-1}$ ($\pm 4$ cm$^{-1}$ for all shifts) for the fibrous tissue and three Raman bands at Raman shifts of 1247-1270, 1449 and 1651 cm$^{-1}$ ($\pm 4$ cm$^{-1}$ for all shifts) for the normal tissue. In addition, it was discovered that the ratios of intensities for the Raman bands at 1659 and 1453 cm$^{-1}$ and at 1254 and 1453 cm$^{-1}$ were 0.69 and 0.53, respectively, for the calcified tissue, 1.02 and 0.85, respectively, for the fibrous tissue and 1.2 and 0.83, respectively, for the normal tissue.

22 Claims, 9 Drawing Sheets

METHOD FOR DISTINGUISHING BETWEEN CALCIFIED ATHEROSCLEROTIC TISSUE AND FIBROUS ATHEROSCLEROTIC TISSUE OR NORMAL CARDIOVASCULAR TISSUE USING RAMAN SPECTROSCOPY

BACKGROUND OF THE INVENTION

The present invention relates to a method for distinguishing between calcified atherosclerotic tissue and fibrous atherosclerotic tissue or normal cardiovascular tissue using Raman spectroscopy.

It is well known that deposits of plaque on cardiovascular tissues, such as on the interior walls of arteries, can severely restrict or completely block the flow of blood therethrough. Such plaque typically exits in two forms, namely, as calcified plaque or as fibrous plaque. Calcified plaque is more rigid and more difficult to remove than fibrous plaque.

As can readily be appreciated, methods for detecting deposits of calcified plaque and/or fibrous plaque on blood vessels have substantial utility in the diagnosis and treatment of atherosclerosis and related cardiovascular ailments.

In U.S. Pat. No. 4,785,806 to Deckelbaum, which is incorporated herein by reference, a process and apparatus for ablating atherosclerotic tissue is disclosed. The process comprises directing a low power ultraviolet laser having a wavelength outside the band of visible wavelengths at a selected section of a blood vessel to cause fluorescence of the tissue in said section, analyzing the frequency spectrum of such fluorescence to determine whether the section of the blood vessel at which said low power laser is directed is normal or atherosclerotic, providing a high power laser having an output in the form of pulses, the pulse duration and pulse energy per unit area of said pulses being selected so as to cause ablation without charring, directing the pulses from said high power laser at said section if said step of analyzing the frequency spectrum indicates that said section is atherosclerotic, continuing to irradiate the tissue with said low power ultraviolet laser energy to cause said tissue to fluoresce, and discontinuing the laser ablation process when the fluorescence pattern of the tissue indicates that it is no longer atherosclerotic.

In U.S. Pat. No. 4,718,417 to Kittrell et al., there is also disclosed a method for diagnosis of the type of tissue in an artery, including distinguishing artery wall from atheromateous plaque using visible fluorescence spectral information.

While the above-described processes are suitable for detecting fibrous atherosclerotic tissue, they cannot be used to detect calcified atherosclerotic tissue since calcified atherosclerotic tissue and normal cardiovascular tissue have indistinguishable fluorescence spectra.

A variety of spectroscopic methods for detecting calcified atherosclerotic tissue are described by R. H. Clarke et al. in "Spectroscopic Characterization of Cardiovascular Tissue," *Lasers in Surgery and Medicine*, Vol. 8, pp. 45-59 (1988). In particular, Clarke et al. discuss using visible Raman spectroscopy to analyze the surface of diseased and healthy tissue sites on postmortem specimens of calcified aortic valve leaflets and coronary artery segments.

In "Raman Spectroscopy of Atherosclerotic Plaque: Implications for Laser Angioplasty," *Radiology*, Vol. 177, pp. 262 (Nov. 1990 Supplement), Redd et al. disclose using visible Raman spectroscopy to analyze human cadaveric aorta, percutaneous peripheral atherectomy, and surgical endarterectomy samples and conclude that Raman spectroscopy allows fatty plaque to be distinguished from a normal artery.

One disadvantage to using visible light to illuminate biological materials for analysis by Raman spectroscopy as described above is that a significant fluorescence background is usually obtained. Consequently, to obtain the Raman spectrum, one must assume the fluorescence profile and subtract it from any observed signal. This method is inaccurate and difficult to use.

In "Applications of Near-Infrared Fourier Transform Raman Spectroscopy in Biology and Medicine," *Spectroscopy*, Vol. 5, No. 7, pp. 24-32 (1990), Nie et al. disclose that fluorescence-free Raman spectra were obtained from pigmented squirrel eye lenses, normal and cataracious human eye lenses, intact bones and teeth, various woody tissues, human and chicken sclera, blood vessels, liver tissue, muscles, cartilage and tobacco mosaic virus using near-infrared Fourier Transform (FT) Raman spectroscopy.

In "Human Breast Tissue Studied by IR Fourier Transform Raman Spectroscopy," *Lasers in the Life Sciences*, Vol. 4, No. 1, pp. 1-6 (1991), Alfano et al. disclose that fluorescence-free Raman spectra of benign breast tissues, benign tumor tissues, and malignant tumor tissues were obtained using IR FT Raman spectroscopy, and note that the difference in the relative intensity between the 1445 and 1651 cm$^{-1}$ Raman lines, as well as the number of Raman lines in the different tissues, offers a potentially new optical diagnostic to detect cancer.

SUMMARY OF THE INVENTION

It is an object of the present invention to provide a new and improved method for distinguishing calcified atherosclerotic tissue from normal cardiovascular tissue.

It is another object of the present invention to provide a method for distinguishing calcified atherosclerotic tissue from fibrous cardiovascular tissue.

It is a further object of the present invention to provide a method as described above which does not require the use of X-ray sensitive plates, photodetectors, fluorescence or ultrasound.

It is still a further object of the present invention to provide a method as described above which does not result in a significant fluorescence background.

It is still yet a further object of the present invention to provide a method as described above which can be used either in vivo or in vitro.

The present invention is based on the surprising discovery that calcified atherosclerotic tissue produces an infrared Fourier Transform Raman spectrum that is distinguishable from infrared Fourier Transform Raman spectra obtained from fibrous atherosclerotic tissue and normal cardiovascular tissue.

As described more fully below, calcified atherosclerotic human aortic tissue, fibrous atherosclerotic human aortic tissue, and normal human aortic tissue were irradiated with monochromatic infrared light and the respective infrared Fourier Transform Raman spectra were obtained. These spectra showed five characteristic Raman bands at Raman shifts of 957, 1071, 1262-1300, 1445, and 1659 cm$^{-1}$ ($\pm 4$ cm$^{-1}$ for all shifts) for the calcified tissue as compared to three characteristic Raman bands at Raman shifts of 1247-1270, 1453, and 1659 cm$^{-1}$ ($\pm 4$ cm$^{-1}$ for all shifts) for the fibrous tissue and three characteristic Raman bands at Raman shifts of about 1247-1270, 1449, and 1651 cm$^{-1}$ ($\pm 4$ cm$^{-1}$ for all shifts) for the normal tissue. In addition, the intensity ratios for each of the tissue types calculated at 1254 cm$^{-1}$ and 1453 cm$^{-1}$ and at 1453 cm$^{-1}$ and 1659 cm$^{-1}$ were about 0.53 and 0.69, respectively, for the calcified tissue as compared to about 0.83 and 1.2, respectively, for the normal tissue and about 0.85 and 1.02, respectively, for the fibrous tissue.

Accordingly, based on the above-noted discovery, a method for distinguishing between calcified atherosclerotic tissue and fibrous atherosclerotic tissue or normal cardiovascular tissue comprises in one embodiment irradiating a cardiovascular tissue sample with a beam of infrared monochromatic light, obtaining the infrared Raman spectrum for the cardiovascular tissue sample, and comparing said infrared Raman spectrum with standard infrared Raman spectra from calcified atherosclerotic tissue and from either fibrous atherosclerotic tissue or normal cardiovascular tissue for the same type of cardiovascular tissue being tested.

In another embodiment, a method for distinguishing between calcified atherosclerotic tissue and fibrous atherosclerotic tissue or normal cardiovascular tissue comprises irradiating a cardiovascular tissue sample with a beam of infrared monochromatic light, measuring the intensity of two characteristic Raman bands common to the infrared Raman spectra for calcified atherosclerotic tissue and fibrous atherosclerotic tissue or normal cardiovascular tissue for the same type of cardiovascular tissue being tested, calculating the ratio of said intensities, and comparing said ratio to the respective ratios for calcified atherosclerotic tissue and for fibrous atherosclerotic tissue or normal cardiovascular tissue for the same type of cardiovascular tissue being tested.

The foregoing and other objects and advantages will appear from the description to follow. In the description, reference is made to the accompanying drawing which forms a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

DETAILED DESCRIPTION OF PREFERRED EMBODIMENTS

The present invention is directed to a method for distinguishing between calcified atherosclerotic tissue and fibrous atherosclerotic tissue or normal cardiovascular tissue.

The present invention is based on the above-noted discovery that, when irradiated with a beam of monochromatic infrared light, calcified atherosclerotic tissue produces a Fourier Transform Raman spectrum that is distinguishable from analogous spectra obtained from fibrous atherosclerotic tissue and normal cardiovascular tissue. Therefore, by comparing the infrared Raman spectrum from a tissue sample whose condition is unknown with standard infrared Raman spectra obtained from calcified atherosclerotic tissue and from fibrous atherosclerotic tissue or normal cardiovascular tissue for the same type of tissue being tested (e.g., human aortic tissue is compared to human aortic tissue standards), it is possible to determine if the tissue sample is calcified atherosclerotic, on one hand, or fibrous atherosclerotic or normal, on the other hand. The types of comparisons that can be made to come this determination are numerous. For example, one can compare the number of characteristic Raman lines in the spectrum for the tissue sample with the number of characteristic Raman lines in the standard spectra. As another example, one can compare the ratio of intensities of two characteristic Raman lines which are common to the spectra for the tissue in its calcified atherosclerotic and fibrous atherosclerotic or normal states with the respective ratios for calcified atherosclerotic tissue and fibrous atherosclerotic tissue or normal tissue for the same of type of tissue being tested.

Figure 1:
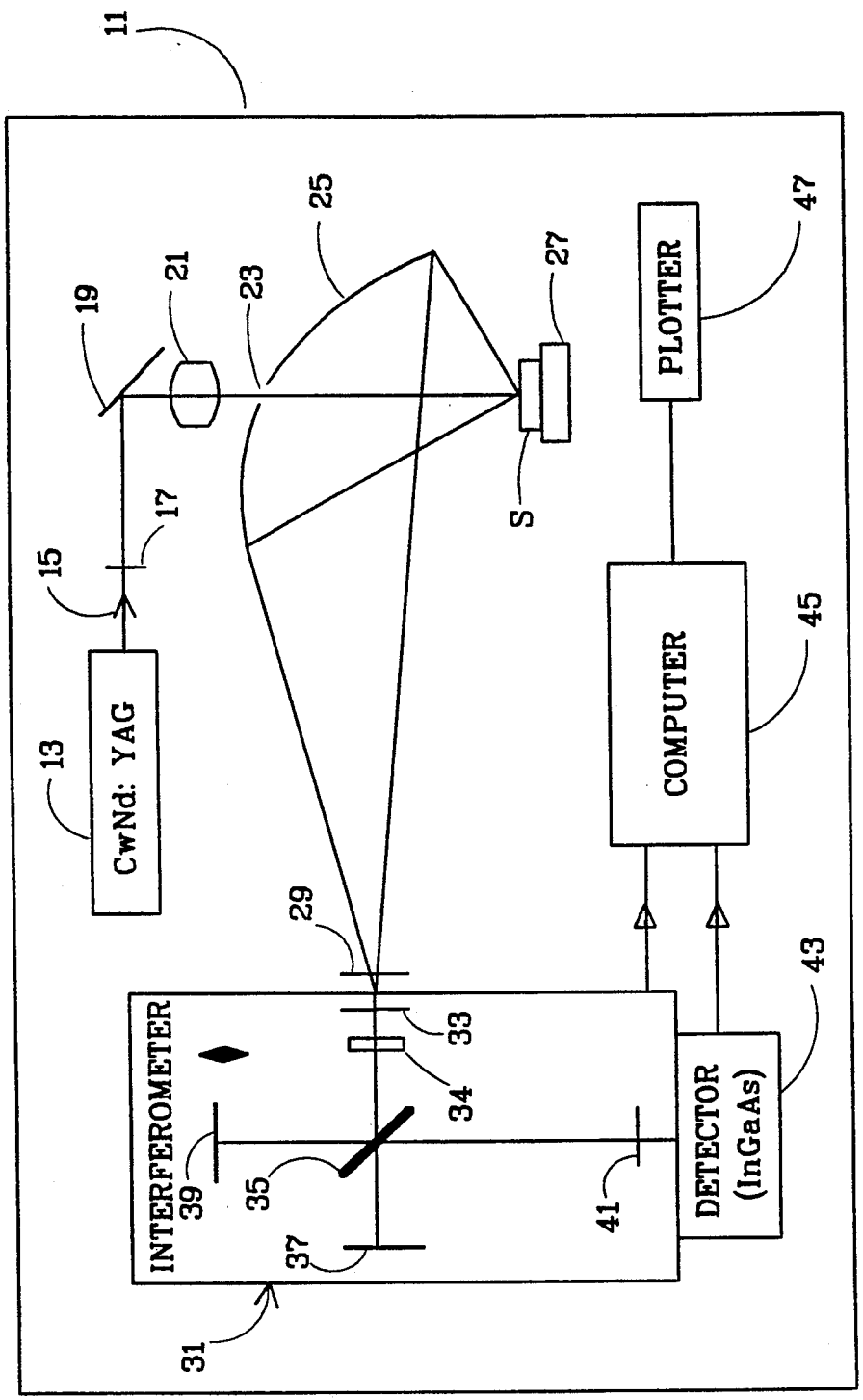
FIG. 1 is a schematic diagram of an infrared Fourier Transform Raman spectroscopy system which can be used to perform the method of the present invention.

Referring now to FIG. 1, there is shown a schematic diagram of a system which was used to perform the method of the present invention, the system being represented generally by reference numeral 11.

System 11 includes a laser 13 for generating a beam of monochromatic infrared light 15. Laser 13 may be any infrared laser capable of emitting light at about 680–1350 nanometers (nm). For example, laser 13 may be a semiconductor, fosterite, YAG, Ti sapphire, alexandrite nitrogen, emerald, GGSG or dye laser and can also be used with harmonic generators for second and third harmonic generations. Preferably, laser 13 is a Quantronix model 114 Nd:YAG laser producing unpolarized TEM$_{00}$ infrared radiation at 1064 nm of about 1 watt power.

Beam 15 passes through a combination narrow-band, wide-band, and neutral density filter unit 17, is reflected off a mirror 19 and is focused by a lens 21 through a hole 23 in an on-axis ellipsoidal mirror 25 onto a sample S, which is mounted on a holder 27. Preferably holder 27 is a three-dimensional adjustable slide in a glass tube. Upon striking sample S, the beam of light is scattered in accordance with the Raman effect. The scattered light strikes ellipsoidal mirror 25, where it is collected and brought to focus onto a filter 29, which blocks out radiation at 1064 nm at the entrance to a conventional Michelson interferometer 31. On entering interferometer 31, the beam passes through a filter 33 which is further constructed to block out radiation at 1064 nm. Next, the beam is collimated by a collimator 34 and then split into two beams by a $CaF_2$ beam splitter 35. One beam is reflected off a fixed mirror 37, and the other beam is reflected off a movable mirror 39. The two beams are recombined at beam splitter 35 and pass through a neutral density filter 41.

The resultant interference pattern produced by interferometer 31 is detected with a liquid nitrogen-cooled indium-gallium-arsenide photodiode-type detector 43. The information is then processed with a computer 45 and displayed as a Raman spectrum on a plotter 47.

System 11 may comprise a modified Bomem DA 3.16 FT-Raman spectrophotometer, distributed by Bomem, Inc. having a place of business in Newark, Del.

Three calcified atherosclerotic human aortic tissue specimens, three fibrous atherosclerotic human aortic tissue specimens, and three normal human aortic tissue specimens were analyzed with system 11. (Histology of the tissue specimens were performed before the measurements.) Each specimen was cut into a section 6×6 mm in size. For each specimen, 2-3 sites were measured. For each measurement, the specimen was irradiated for 12 minutes with light having a power density of about 10 watt/$cm^2$. The Raman spectral region from 700 to 1900 $cm^{-1}$ was measured at room temperature. The results of these measurements are displayed in the Table, and representative spectra for calcified atherosclerotic human aortic tissue, fibrous atherosclerotic human aortic tissue, and normal human aortic tissue are depicted in FIGS. 2 through 4, respectively.

Figure 2:
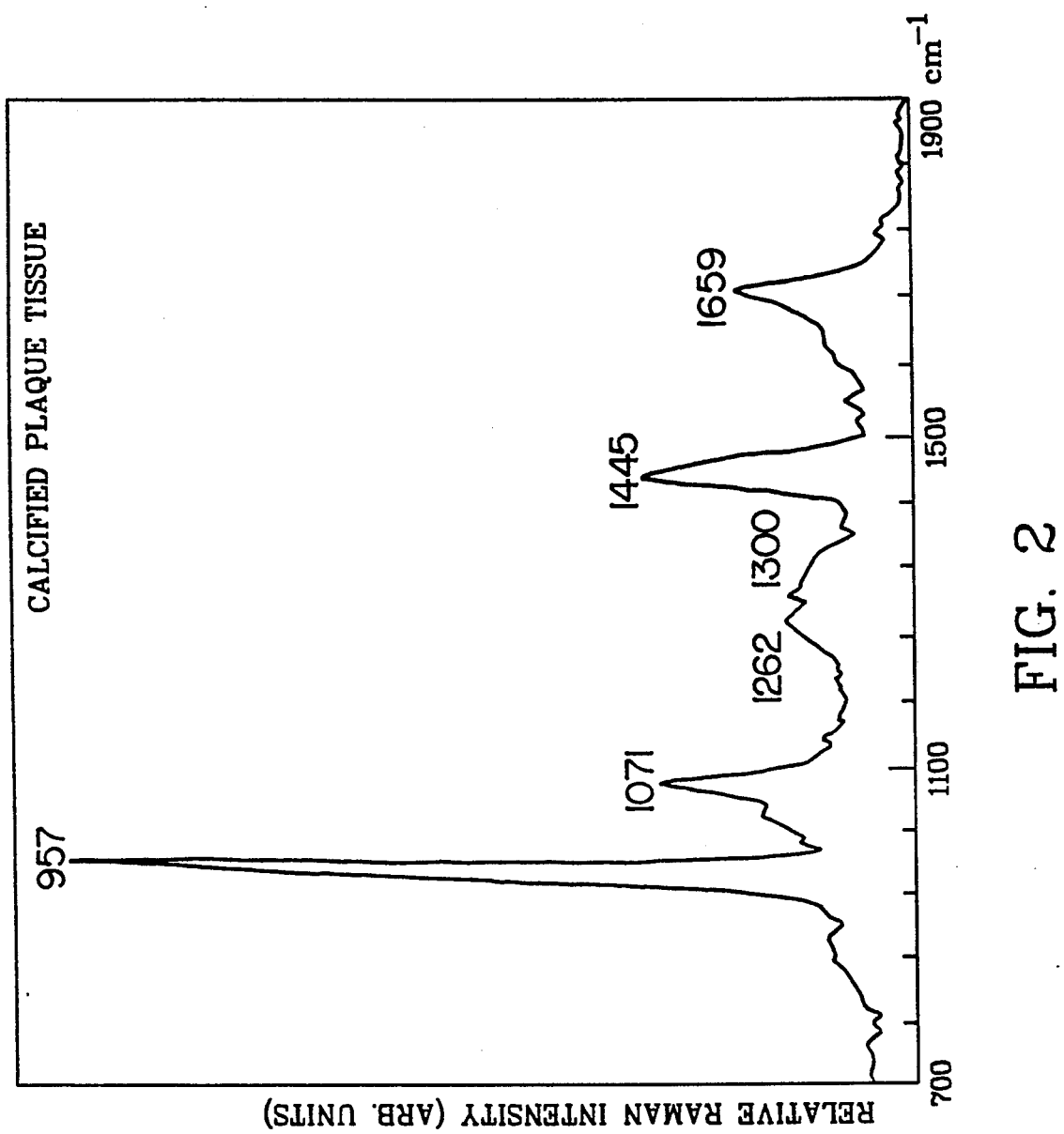
FIG. 2 is an infrared Fourier Transform Raman spectrum obtained from calcified atherosclerotic human aortic tissue.
Figure 3:
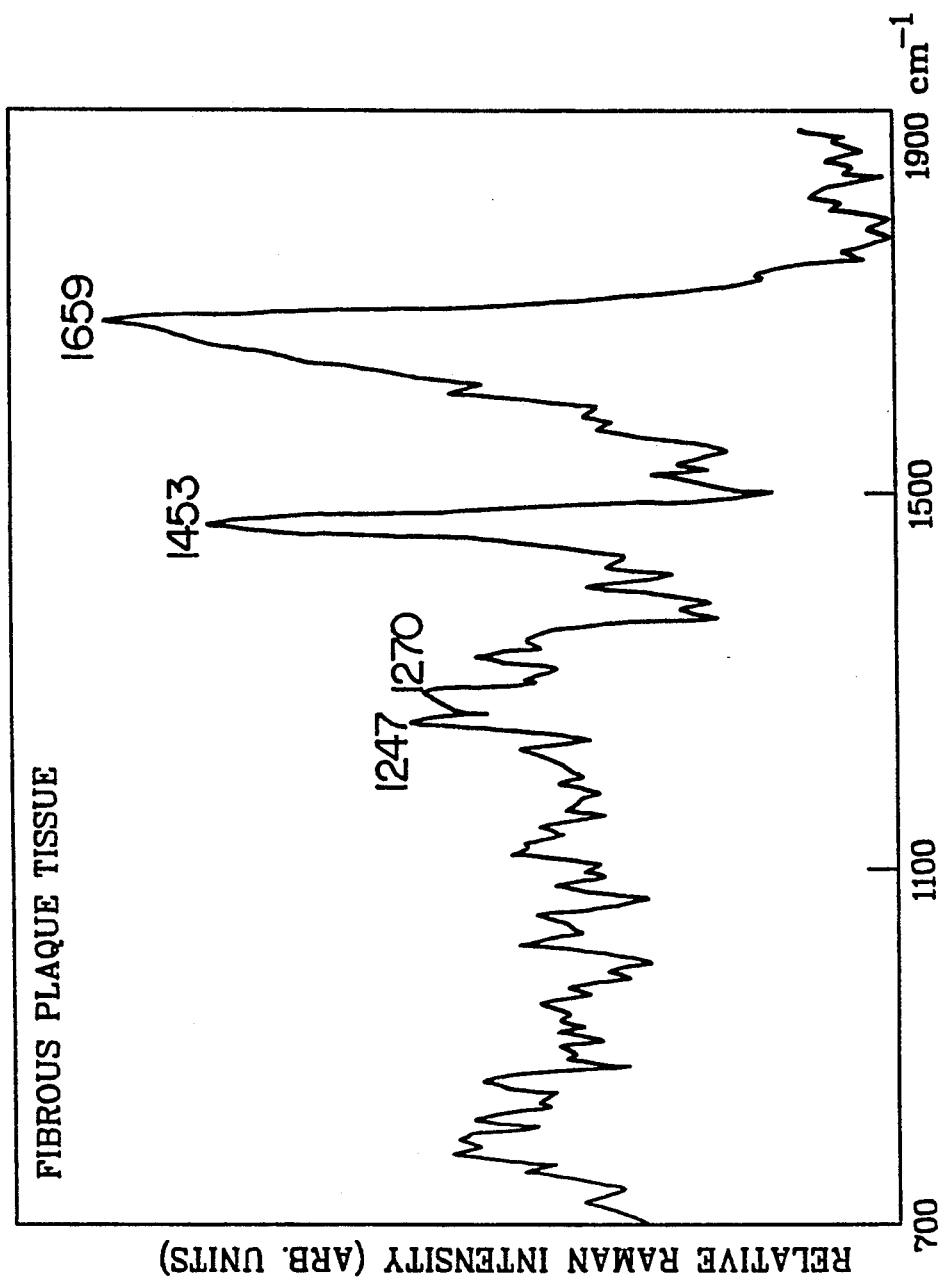
FIG. 3 is an infrared Fourier Transform Raman spectrum obtained from fibrous atherosclerotic human aortic tissue.
Figure 4:
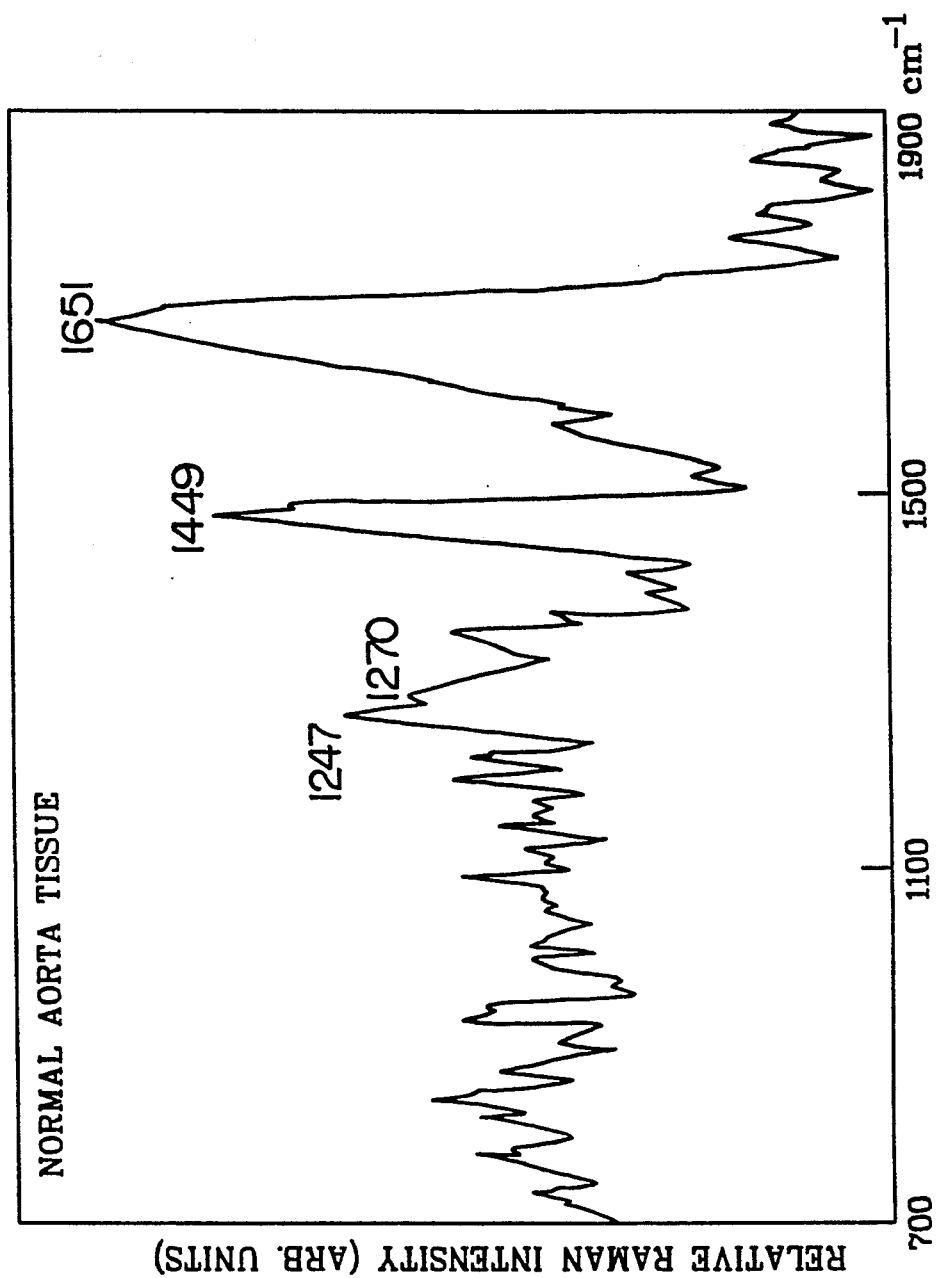
Fig. 4 is an infrared Fourier Transform Raman spectrum obtained from normal human aortic tissue.

As can be seen from the Table and in FIGS. 2 through 4, the spectrum for calcified tissue is characterized by five Raman bands at Raman shifts of 957, 1071, 1262-1300, 1445, and 1659 $cm^{-1}$ ($\pm 4$ $cm^{-1}$ for are shifts) whereas the spectrum for fibrous tissue is characterized by three Raman bands at Raman shifts of 1247-1270, 1453, and 1659 $cm^{-1}$ ($\pm 4$ $cm^{-1}$ for all shifts) and the spectrum for normal tissue is characterized by three Raman bands at Raman shifts of 1247-1270, 1449 and 1651 $cm^{-1}$ ($\pm 4$ $cm^{-1}$ for all shifts). Consequently, it is possible to characterize a human aortic tissue sample as being, on one hand, calcified atherosclerotic or, on the other hand, fibrous atherosclerotic or normal, by noting, for example, whether five or three Raman bands appear in its spectrum or by noting, for example, whether certain Raman bands appear in the spectrum, such as the 957 $cm^{-1}$ band and/or the 1071 $cm^{-1}$ band, which appear only with calcified tissue.

As can also be seen from the Table, the ratio of intensities of the three common Raman bands provides still another basis for distinguishing calcified tissue from fibrous tissue and normal tissue. For example, the ratio of intensities of the Raman bands at Raman shifts of 1659 and 1453 $cm^{-1}$ is about 0.69 for the calcified tissue, about 1.02 for the fibrous tissue, and about 1.2 for the normal tissue. In addition, the ratio of intensities of the Raman bands at Raman shifts of 1254 and 1453 $cm^{-1}$ is about 0.53 for the calcified tissue, about 0.83 for the normal tissue, and about 0.85 for the normal tissue. (The difference in the 1659 $cm^{-1}$:1453 $cm^{-1}$ intensity ratio for fibrous tissue and normal tissue may also be used as a basis for distinguishing fibrous tissue from normal tissue.)

Figure 5:
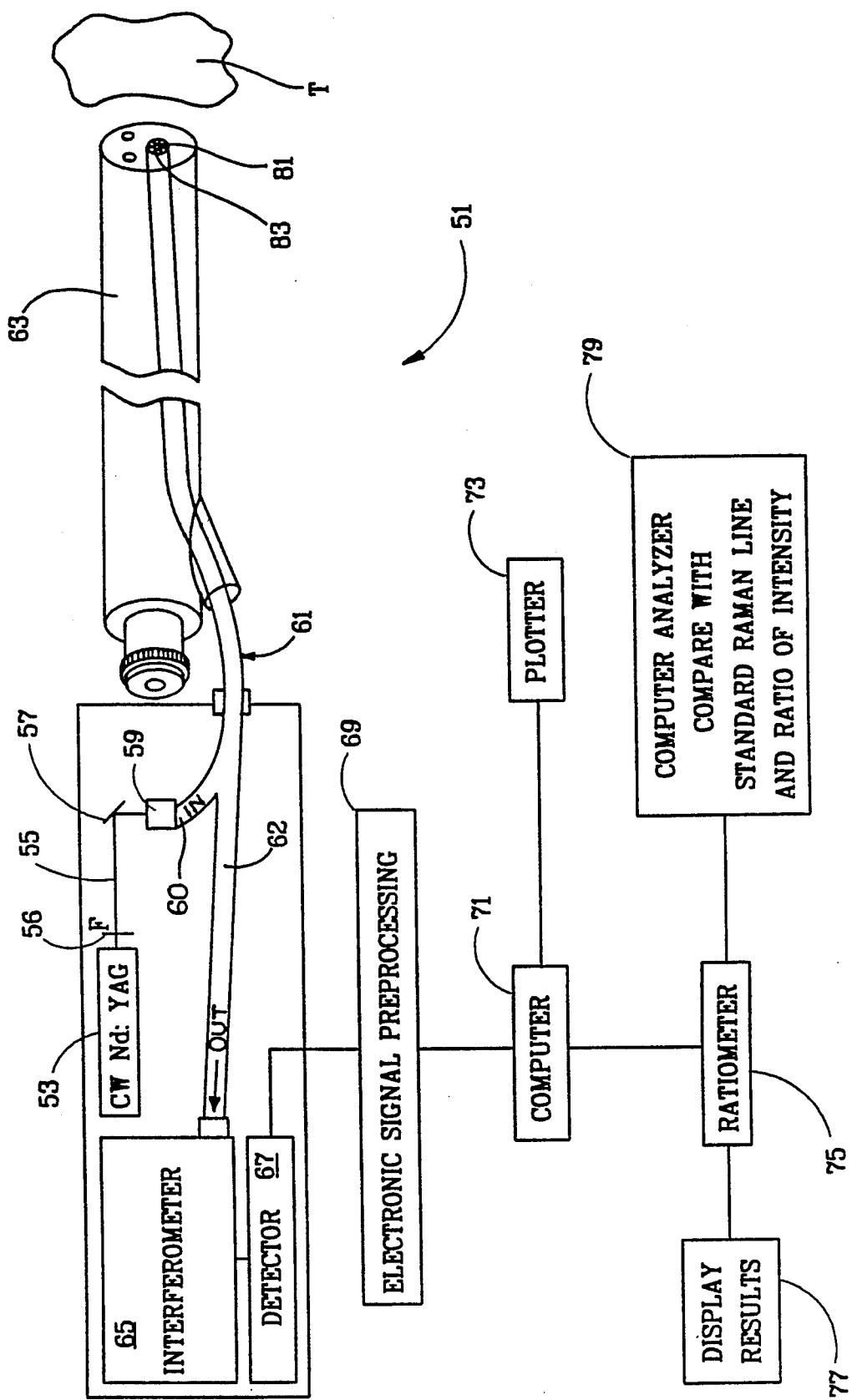
FIG. 5 is a schematic diagram of one embodiment of a system adapted for in vivo or in vitro testing of a sample tissue, the system being constructed according to the teachings of the present invention.

Referring now to FIG. 5, there is shown an embodiment of a system for in vivo or in vitro testing of a cardiovascular tissue sample to determine if the cardiovascular tissue sample is calcified atherosclerotic, on one hand, or fibrous atherosclerotic or normal, on the other hand, the system being constructed according to the teachings of the present invention and represented generally by reference numeral 51.

System 51 includes a laser 53, such as a continuous wave Nd:YAG laser, for producing a beam 55 of monochromatic infrared light. Beam 55 first passes through a combination narrow-band, wide-band, neutral density filter unit 56. Next, beam 55 is reflected off a mirror 57 and passes through a lens coupler 59 into an input leg 60 of a bifurcated optical fiber bundle assembly 61 disposed within a probe, which is in the form of an endo-

TABLE

Differences in Raman Spectra between 700 and 1900 $cm^{-1}$
for Calcified Atherosclerotic Human Aortic Tissue, Fibrous
Atherosclerotic Human Aortic Tissue, and Normal Human Aortic
Tissue

| | Calcified Tissue | Normal Tissue | Fibrous Tissue |
|---|---|---|---|
| No of Samples Measured | 3 | 3 | 3 |
| Measured Sites | 9 | 8 | 9 |
| Characteristic Raman Vibrational Frequency ($\pm 4$ $cm^{-1}$) | 957 1071 1262-1300 1445 1659 | 1247-1270 1449 1651 | 1247-1270 1453 1659 |
| Relative Intensity | $I_{(957)} > I_{(1071)} > I_{(1254)} < I_{(1453)} > I_{(1659)}$ | $I_{(1247)} < I_{(1449)} < I_{(1651)}$ | $I_{(1270)} < I_{(1453)} < I_{(1659)}$ |
| Ratio of Intensity ($\pm 0.03$) | $I_{(957)}:I_{(1071)}:I_{(1254)}:I_{(1453)}:I_{(1659)}$ 3.08:0.97:0.53:1.00:0.69 | $I_{(1254)}:I_{(1453)}:I_{(1659)}$ 0.83:1.00:1.20 | $I_{(1254)}:I_{(1453)}:I_{(1659)}$ 0.85:1.00:1.02 | scope 63. The light strikes the tissue T being tested and produces Raman scattering. The scattered light is then transmitted back through an output leg 62 of assembly 61 to a Michelson interferometer 65. The interferogram produced by the interferometer is then detected by detector 67 and transmitted to an electronic signal preprocessing unit 69, which interfaces detector 67 to a computer 71. The output of computer 71 is then sent either to a plotter 73, which plots the Raman spectrum, or to a ratiometer 75, which calculates the ratio of intensities at two common characteristic Raman lines, such as the Raman bands at a Raman shift of about 1453 and 1659 cm$^{-1}$ in the case of human aortic tissue. The output from ratiometer 75 is then sent either to a display 77 or to a computer analyzer 79, which compares the intensity ratio for the tissue being tested with standard ratios from calcified atherosclerotic tissue and from fibrous atherosclerotic tissue or normal tissue for the same type of tissue being tested.

Figure 7:
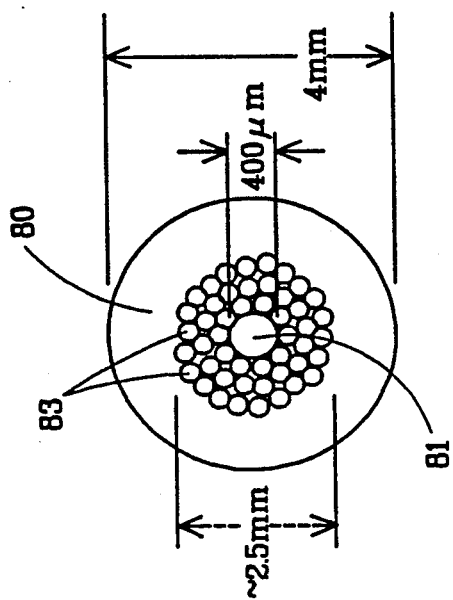
FIG. 7 is an enlarged section view taken along the line AA of the optical fiber bundle shown in FIG. 6.
Figure 6:
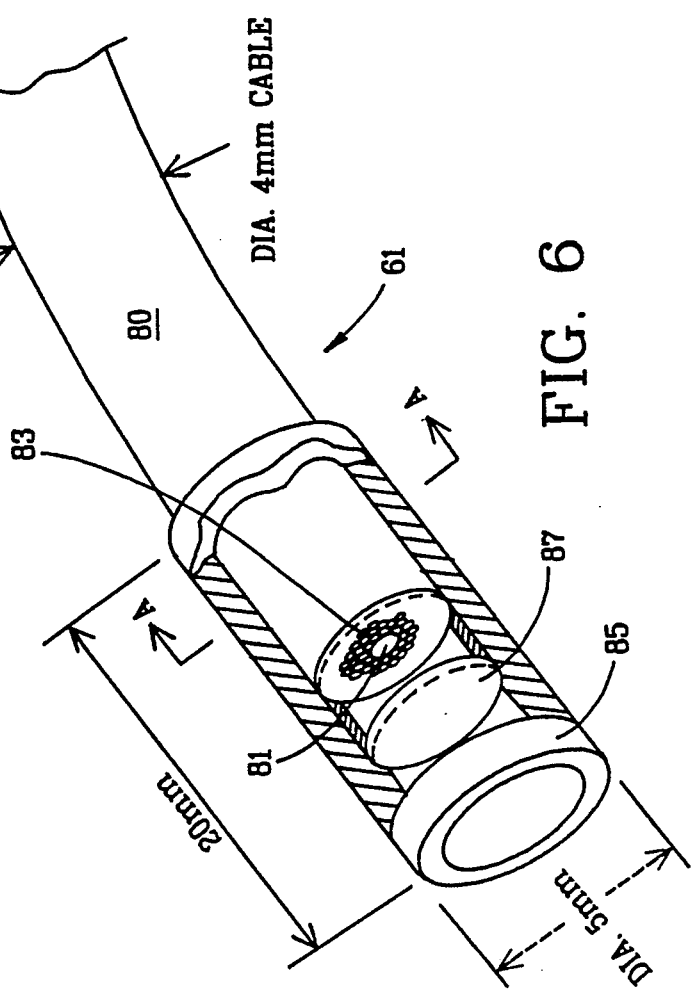
FIG. 6 is an enlarged perspective view, broken away in part, of the optical fiber bundle assembly shown in FIG. 5.

Referring now to FIG. 6, there is shown an enlarged perspective view, broken away in part, of optical fiber bundle assembly 61. Assembly 61 includes a cable 80. Cable 80, which has an outer diameter of 4 mm, houses a number of optical fibers 81 and 83 made of quartz, sapphire or any other infrared-transmitting material. Fiber 81, which is centrally disposed in cable 80, has a diameter of about 400 um. Fiber 81 conveys the beam of infrared monochromatic light to the tissue being tested. Optical fibers 83, each having a diameter of about 100 to 200 um, surround fiber 81. Fibers 83 convey the Raman scattered light from the tissue being tested to the interferometer. Fibers 81 and 83, taken together, have a diameter of about 2.5 to 4.0 mm (see FIG. 7).

Assembly 61 also includes a housing 85, which is glued to the end of cable 80. Housing 85, which is about 20 mm in length and about 5 mm in diameter, is preferably made of metal. If desired, a focusing lens 87 for focusing the light entering and leaving the optical fibers may be mounted within housing 85. Lens 87, which is made of quartz or sapphire, is preferably 3 mm in diameter and has a focal length of 7 mm.

Figure 8:
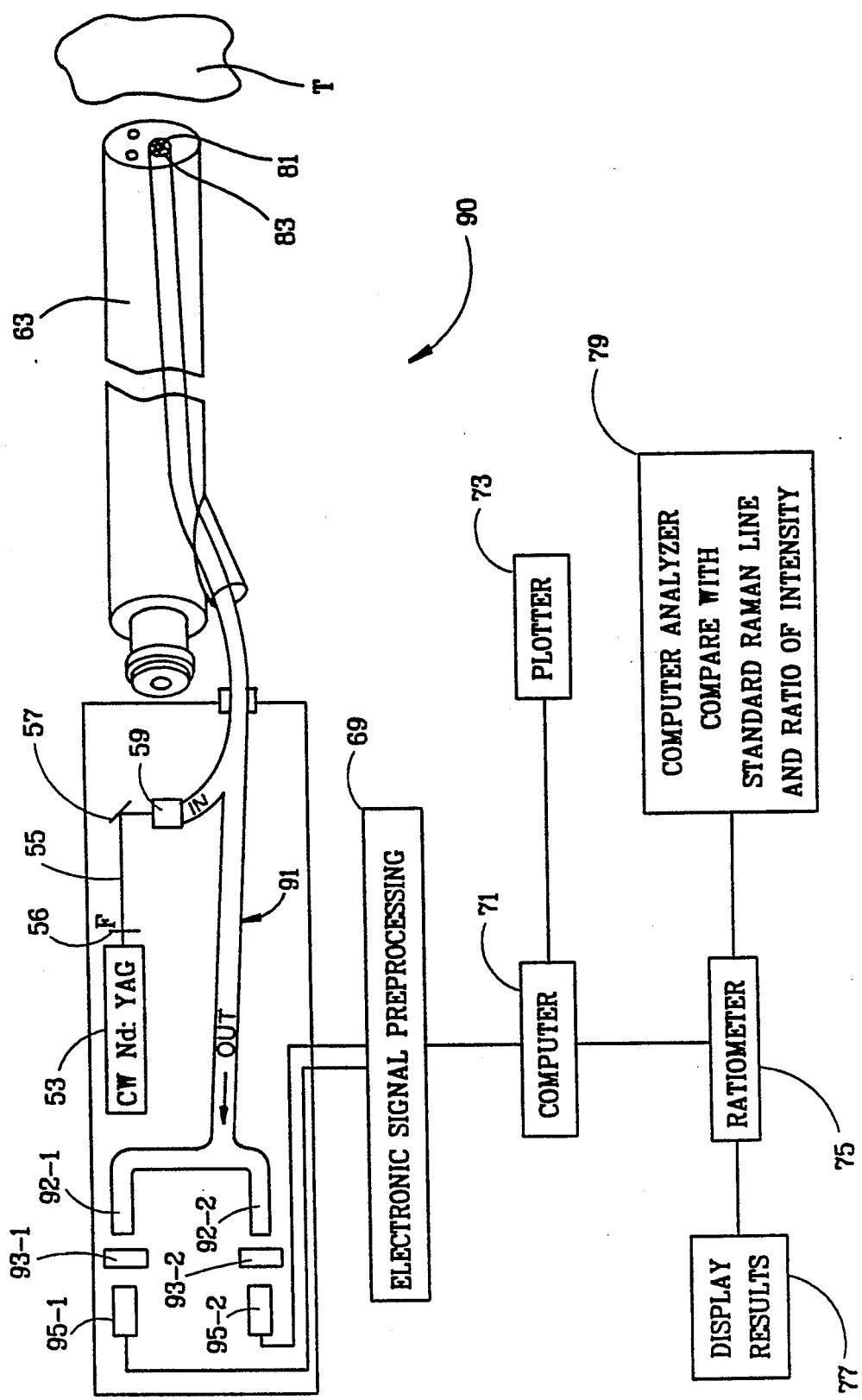
FIG. 8 is a schematic diagram of a second embodiment of a system adapted for in vivo or in vitro testing of a sample tissue, the system being constructed according to the teachings of the present invention.

Referring now to FIG. 8, there is shown a second embodiment of a system for in vivo or in vitro testing of a cardiovascular tissue sample to determine if the tissue sample is calcified atherosclerotic as compared to fibrous atherosclerotic or normal, the system being constructed according to the teachings of the present invention and represented generally by reference numeral 90.

System 90 is constructed in generally the same manner as system 51. However, system 90 includes an optical fiber bundle assembly having an output leg 91 which is bifurcated into two output legs 92-1 and 92-2. Light emerging from output legs 92-1 and 92-2 is passed through a pair of narrow band filters 93-1 and 93-2, which have a bandwidth of less than about 10 nm and are designed to pass light at wavelengths $\lambda_1$ and $\lambda_2$, respectively. The light passing through filters 93-1 and 93-2 then impinges on a pair of photodetectors 95-1 and 95-2. Photodetectors 95-1 and 95-2 are conventional photodetectors having maximum sensitivity in the regions of interest, namely, at wavelengths $\lambda_1$ and $\lambda_2$, respectively. The outputs of photodetectors 95-1 and 95-2 are fed into electronic signal preprocessing unit 69.

The values of wavelengths $\lambda_1$ and $\lambda_2$ are equal to $(1/\lambda_0 - v_1)^{-1}$ and $(1/\lambda_0 - v_2)^{-1}$, respectively, wherein $\lambda_0$ is the wavelength of light emitted by laser 53 and wherein $v_1$ and $v_2$ are the wavenumbers of two different Raman shifts for the type of tissue being tested. Preferably, one of the two Raman shifts is common to both calcified atherosclerotic tissue and fibrous atherosclerotic tissue or normal tissue (to serve as a control), and the other of the two Raman shifts is particular to calcified atherosclerotic tissue. For example, in the case of human aortic tissue, $v_1$ and $v_2$ could be 1659 cm$^{-1}$ and 957 cm$^{-1}$, respectively. By selecting the values of $v_1$ and $v_2$ thusly, one can determine if a human aortic tissue sample is calcified atherosclerotic tissue either by noting the presence of light shifted by 957 cm$^{-1}$ or by calculating the ratio of intensities at 957 cm$^{-1}$ and 1659 cm$^{-1}$.

Figure 9:
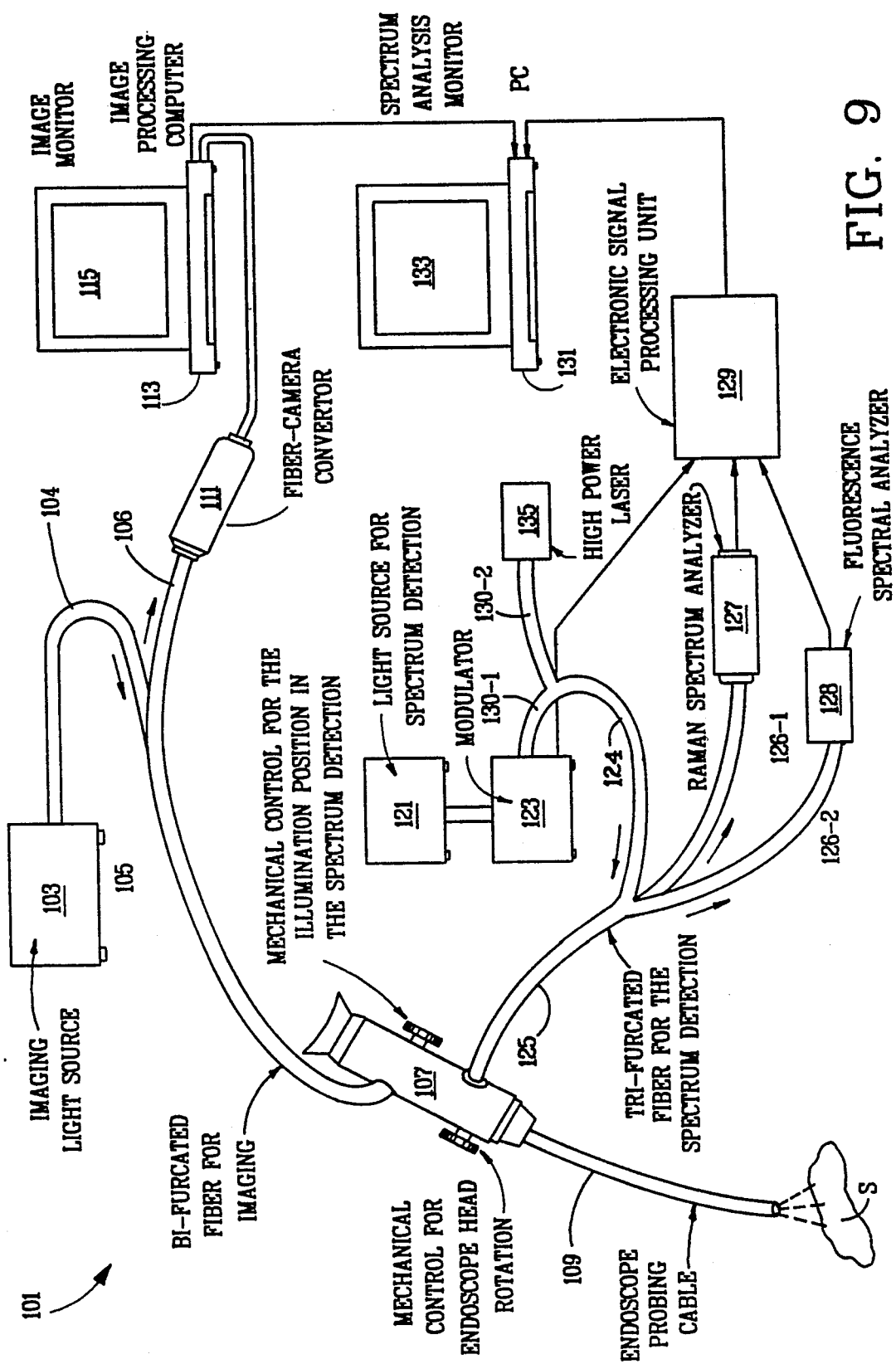
FIG. 9 is a schematic diagram of a third embodiment of a system adapted for in vivo or in vitro testing of a sample tissue, the system being constructed according to the teachings of the present invention.

Referring now to FIG. 9, there is shown an embodiment of a system for in vivo or in vitro testing of a cardiovascular tissue sample to determine if the tissue sample is calcified atherosclerotic, fibrous atherosclerotic, or normal, the system being constructed according to the teachings of the present invention and represented generally by reference numeral 101.

System 101 includes an imaging light source 103. The light produced by source 103 is transmitted through an input leg 104 of a bifurcated optical fiber assembly 105 to an endoscope 107, where it is transmitted through one channel of an endoscope probing cable 109 to the tissue sample S. An image of the tissue sample is then transmitted back through the same channel of cable 109 and transmitted through an output leg 106 of bifurcated fiber assembly 105 to a converter 111. Converter 111 converts the optical image into digital information, which is then transmitted to an image processing computer 113, which processes the information and displays the image on a monitor 115.

System 101 also includes a light source 121. Source 121 produces both infrared light and ultraviolet or visible light, the infrared light being used for Raman detection of calcified atherosclerotic tissue and the ultraviolet or visible light being used for fluorescence detection of fibrous atherosclerotic tissue. The light from source 121 is modulated by a modulator 123 and then transmitted through a first leg 130-1 of a bifurcated input leg 124 of a trifurcated optical fiber assembly 125 to endoscope 107, where it is transmitted through a second channel of endoscope probing cable 109 to the tissue sample. The emerging light from the tissue sample is then transmitted back through the same channel of cable 109 and on through a pair of output legs 126-1 and 126-2. Output leg 126-1 transmits the light to a Raman spectral analyzer 127, which produces a Raman spectrum of the sample and then converts the spectral information into an electronic signal. Output leg 126-2 transmits the light to a fluorescence spectral analyzer 128, which produces a fluorescence spectrum of the sample and then converts the spectral information into an electronic signal. The outputs of analyzers 127 and 128 are then transmitted to an electronic processing unit 129, which interfaces analyzers 127 and 128 to a computer 131. Computer 131 comprises the Raman spectral information and fluorescence spectral information to standards for calcified atherosclerotic tissue, fibrous atherosclerotic tissue, and normal tissue and display the results of the comparison on a monitor 133.

System 101 also includes a high power ultraviolet or visible laser 135 (e.g., YAG laser, Ti sapphire laser, Fosterite laser with second and third harmonic generations) for producing light to ablate atheroscelotic tissue detected in the manner described above. The output of laser 135 is transmitted though a second leg 130-2 of bifurcated input leg 124 to endoscope 107, where it is transmitted through the second channel of cable 109.

Figure 10:
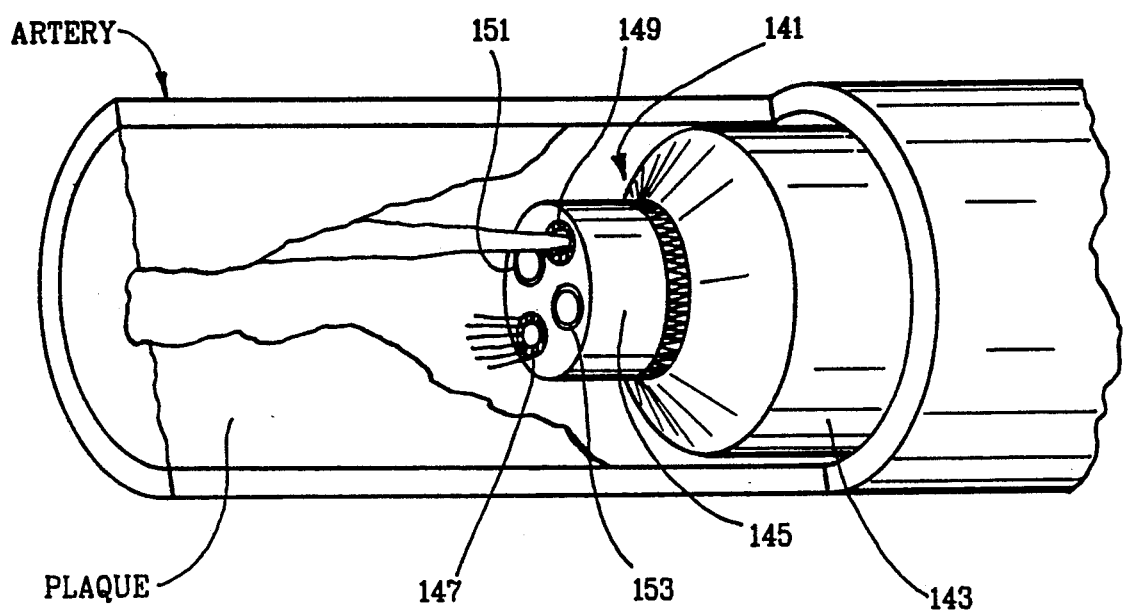
FIG. 10 is a perspective view of an atherosclerotic artery, broken away in part, to reveal an endoscope disposed therein, the endoscope being constructed according to the teachings of the present invention.

Referring now to FIG. 10, there is shown a portion of an atherosclerotic artery, which is broken away in part to reveal a portion of an endoscope disposed therein, the endoscope being constructed according to the teachings of the present invention and represented generally by reference numeral 141.

Endoscope 141 includes an outer cuff 143, which is sized and shaped to fit within an artery or other blood vessel. Cuff 143 surrounds all but the tip of a cable 145, which includes four channels. An optical fiber bundle 147, which is used to illuminate the interior of the artery for imaging on a monitor as in FIG. 8, is mounted within a first channel. A fiber optic bundle 149, which is similar in construction to cable 80 as seen in FIG. 6, is mounted within a second channel. Bundle 149 is used to convey infrared light and fluorescence-inducing light (e.g. ultraviolet light, visible light) to the arterial tissue and to collect the resulting Raman scattered light for use in detecting calcified atherosclerotic tissue and the resulting fluorescence for use in detecting fibrous atherosclerotic tissue, respectively. An optical fiber 151, which is used to transmit powerful laser light to any detected atherosclerotic tissue for ablation, is mounted within a third channel. A length of tubing 153 for use in aspirating ablated tissue and other debris from the artery is mounted within a fourth channel.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for distinguishing between calcified atherosclerotic tissue and fibrous atherosclerotic tissue or normal cardiovascular tissue comprising the steps of:
    a) irradiating a cardiovascular tissue sample with a beam of monochromatic infrared light;
    b) obtaining the infrared Raman spectrum for the cardiovascular tissue sample in the Raman spectral region from 700 to 1900 cm$^{-1}$; and
    c) comparing the infrared Raman spectrum so obtained for the tissue sample with infrared Raman spectra correspondingly obtained from known samples of calcified atherosclerotic tissue and from either fibrous atherosclertoic tissue or normal cardiovascular tissue for the same type of tissue being tested.

2. The method of claim 1 wherein the cardiovascular tissue being tested is human cardiovascular tissue.

3. The method of claim 2 wherein the human cardiovascular tissue is human aortic tissue.

4. A method of determining if a cardiovascular tissue sample is calcified atherosclerotic, on one hand, or fibrous atherosclerotic or normal, on the other hand, comprising the steps of:
    a) irradiating the cardiovascular tissue sample with a beam of infrared monochromatic light;
    b) measuring the number of Raman bands produced thereby in the Raman spectral region from 700 to 1900 cm$^{-1}$; and
    c) comparing the number of Raman bands measured with the number of Raman bands correspondingly measured from known samples of calcified atherosclerotic tissue and fibrous atherosclerotic tissue or normal cardiovascular tissue for the same type of tissue being tested.

5. The method of claim 4 wherein the tissue being tested is human aortic tissue and wherein the number of Raman bands is five for calcified atherosclerotic and three for fibrous atherosclerotic tissue and normal tissue.

6. A method of determining if a human aortic tissue sample is calcified atherosclerotic, on the one hand, or fibrous atherosclerotic or normal, on the other hand, comprising the steps of:
    a) irradiating the human aortic tissue sample with a beam of infrared monochromatic light;
    b) measuring for a Raman band at 957±4 cm$^{-1}$, or for a Raman band at 1071±4 cm$^{-1}$, or for a pair of Raman bands at 957±4 cm$^{-1}$ and 1071±4 cm$^{-1}$;
    c) whereby the presence of a Raman band at 957±4 cm$^{-1}$, or a Raman band at 1071±4 cm$^{-1}$, or a pair of Raman bands at 957±4 cm$^{-1}$ and 1071±4 cm$^{-1}$, respectively, indicates that the human aortic tissue sample is calcified atherosclerotic and the absence of a Raman band at 957±4 cm$^{-1}$, or at 1071±4 cm$^{-1}$, or at both 957±4 cm$^{-1}$ and 1071±4 cm$^{-1}$ indicates that the human aortic tissue sample is either fibrous atherosclerotic or normal.

7. A method for determining whether a cardiovascular tissue sample is calcified atherosclerotic tissue as compared to fibrous atherosclerotic tissue or normal cardiovascular tissue comprising the steps of:
    a) irradiating the cardiovascular tissue sample with a beam of infrared monochromatic light;
    b) measuring the intensity of light at a pair of Raman bands in the Raman spectral region from 700 to 1900 cm$^{-1}$ which are correspondingly present in the infrared Raman spectra of calcified atherosclerotic tissue and fibrous atherosclerotic tissue or of calcified atherosclerotic tissue and normal cardiovascular tissue for the same type of tissue being tested;
    c) calculating the ratio of said intensities; and
    d) comparing said ratio to the respective ratios for calcified atherosclerotic tissue and fibrous atherosclerotic tissue or for calcified atherosclerotic tissue and normal cardiovascular tissue for the same type of tissue being tested.

8. The method as claimed in claim 7 further comprising the steps of:
    a) irradiating the cardiovascular tissue sample with a beam of fluorescence inducing light;
    b) obtaining a fluorescence spectrum for the cardiovascular tissue sample;
    c) comparing said fluorescence spectrum with standard fluorescence spectra for fibrous atherosclerotic tissue and calcified atherosclerotic tissue or normal tissue for the same type of tissue being tested.

9. The method as claimed in claim 7 wherein said cardiovascular tissue sample is human aortic tissue.

10. A method for determining whether a human aortic tissue sample is calcified atherosclerotic tissue as compared to fibrous atherosclerotic tissue or normal cardiovascular tissue comprising the steps of:
    a) irradiating the cardiovascular tissue sample with a beam of infrared monochromatic light;
    b) measuring the intensity of light at 1659 and 1453 cm$^{-1}$;
    c) calculating the ratio of said intensities; and d) comparing said ratio to the respective ratios for calcified atherosclerotic tissue and fibrous atherosclerotic tissue or for calcified atherosclerotic tissue and normal cardiovascular tissue for the same type of tissue being tested.

11. A method for determining whether a human aortic tissue sample is calcified atherosclerotic tissue as compared to fibrous atherosclerotic tissue or normal cardiovascular tissue comprising the steps of:
   a) irradiating the cardiovascular tissue sample with a beam of infrared monochromatic light;
   b) measuring the intensity of light at 1254 and 1453 cm$^{-1}$;
   c) calculating the ratio of said intensities; and
   d) comparing said ratio to the respective ratios for calcified atherosclerotic tissue and fibrous atherosclerotic tissue or for calcified atherosclerotic tissue and normal cardiovascular tissue for the same type of tissue being tested.

12. A method for determining if a human aortic tissue sample is calcified atherosclerotic as compared to fibrous atherosclerotic or normal, comprising the steps of:
   a) irradiating the human aortic tissue sample with a monochromatic beam of infrared light;
   b) measuring for the presence of a first Raman band having a peak at 957±4 cm$^{-1}$ and a second Raman band having a peak at 1659±4 cm$^{-1}$ or 1651±4 cm$^{-1}$;
   c) whereby the presence of said first Raman band and said second Raman band indicates that the human aortic tissue sample is calcified atherosclerotic, and the absence of said first Raman band and the presence of said second Raman band indicates that the human aortic tissue sample is fibrous atherosclerotic or normal.

13. A method for determining if a human aortic tissue sample is calcified atherosclerotic as compared to fibrous atherosclerotic or normal, comprising the steps of:
   a) irradiating the human aortic tissue sample with a monochromatic beam of infrared light;
   b) measuring the intensity of Raman scattered light at a Raman shift of about 957 cm$^{-1}$ and at a Raman shift of about 1659 cm$^{-1}$;
   c) calculating the ratio of intensities for the Raman scattered light at a Raman shift of about 957 cm$^{-1}$ and at a Raman shift of about 1659 cm$^{-1}$;
   d) comparing said ratio to the respective ratios for calcified atherosclerotic human aortic tissue and for fibrous atherosclerotic human aortic tissue or normal human aortic tissue.

14. A system for determining if a cardiovascular tissue sample is calcified atherosclerotic as compared to fibrous atherosclerotic or normal, comprising:
   a) means for producing an infrared monochromatic beam of light having a wavelength 0;
   b) means for directing said infrared monochromatic beam to the cardiovascular tissue sample;
   c) means for collecting the Raman scattered light from the cardiovascular tissue sample in the Roman spectrum region from 700 to 1900 cm$^1$;
   d) a pair of narrow band filter optically coupled to said collecting means, the first of said narrow band filter being selective for the Raman scattered light at a wavelength $\lambda_1$ wherein $\lambda_1=(1/\lambda_0-v_1)^{-1}$ and wherein $v_1$ is the wavenumber of a Raman shift common to the Raman spectra for calcified atherosclerotic tissue and fibrous atherosclerotic tissue or normal tissue for the same type of tissue being tested, the second of said narrow band filter being selective for the Raman scattered light at a wavelength $\lambda_2$ wherein $\lambda_2=(1/\lambda_0-v_2)^{-1}$ and wherein $v_2$ is the wavenumber of a Raman shift particular to the Raman spectrum for calcified atherosclerotic tissue;
   e) a pair of photodetectors, the first of said photodetectors being optically coupled to the output of said first narrow band filter means for converting the Raman scattered light incident thereon into a first electrical signal and the second of said photodetectors being optically coupled to the output of said second narrow band filter means for converting the Raman scattered light incident thereon into a second electrical signal;
   f) means coupled to the outputs of said photodetectors for determining, based on said electrical signals, whether the cardiovascular tissue sample is calcified atherosclerotic as compared to fibrous atherosclerotic or normal; and
   g) means for displaying the results of said determination.

15. A system for determining if a cardiovascular tissue sample is calcified atherosclerotic tissue as compared to fibrous atherosclerotic tissue or normal cardiovascular tissue, the system comprising:
   a) means for producing an imaging light;
   b) means for producing a beam of monochromatic infrared light;
   c) an endoscope comprising in a first channel means for transmitting said imaging light to the cardiovascular tissue sample and for collecting an image of the cardiovascular tissue sample and in a second channel means for transmitting said beam of monochromatic infrared light to the cardiovascular tissue sample and for collecting the Raman scattered light from the cardiovascular tissue sample in the Raman spectrum region from 700 to 1900 cm$^1$;
   d) means, coupled to said image collection means, for displaying said image of the cardiovascular tissue sample;
   e) means, coupled to said Raman scattered light collection means, for producing a Raman spectrum for the cardiovascular tissue sample;
   f) means for comparing said Raman spectrum to standard Raman spectra for calcified atherosclerotic tissue and for either fibrous atherosclerotic tissue or normal cardiovascular tissue for the same type of cardiovascular tissue being tested; and
   g) means for displaying the results of the comparison.

16. A system for determining if a cardiovascular tissue sample is calcified atherosclerotic tissue as compared to fibrous atherosclerotic tissue or normal cardiovascular tissue, the system comprising:
   a) means for producing an imaging light;
   b) means for producing a beam of monochromatic infrared light;
   c) and endoscope comprising in a first channel means for transmitting said imaging light to the cardiovascular tissue sample and for collecting an image of the cardiovascular tissue sample and in a second channel means for transmitting said beam of monochromatic infrared light to the cardiovascular tissue sample and for collecting the Raman scattered light from the cardiovascular tissue sample in the Raman spectral region from 700 to 1900 cm;

d) means, coupled to said image collection means, for displaying said image of the cardiovascular tissue sample;

e) means, coupled to said Raman scattered light collection means, for producing a Raman spectrum for the cardiovascular tissue sample;

f) means for calculating the ratio of intensities of light at two Raman bands common to the infrared Raman spectra for calcified atherosclerotic tissue and fibrous atherosclerotic tissue or normal cardiovascular tissue for the same type of tissue being tested;

g) means for comparing said ratio to the respective ratios for calcified atherosclerotic tissue and for either fibrous atherosclerotic tissue or normal cardiovascular tissue for the same type of cardiovascular tissue being tested; and h) means for displaying the results of the comparison.

17. A method for determining if a cardiovascular tissue sample is calcified atherosclerotic, fibrous atherosclerotic, or normal, comprising the steps of:

a) irradiating the cardiovascular tissue sample with a monochromatic beam of infrared light;

b) irradiating the cardiovascular tissue sample with a monochromatic beam of fluorescence inducing light;

c) obtaining the infrared Raman spectrum for the cardiovascular tissue sample;

d) obtaining the fluorescence spectrum for the cardiovascular tissue sample;

e) comparing said infrared Raman spectrum with standard infrared Raman spectra for calcified atherosclerotic tissue and for either fibrous atherosclerotic tissue or normal tissue for the same type of tissue being tested; and f) comparing said fluorescence spectrum for the cardiovascular tissue sample with standard fluorescence spectra for fibrous atherosclerotic tissue and for either calcified atherosclerotic tissue or normal tissue for the same type of tissue being tested.

18. The method as claimed in claim 17 further comprising the step of ablating the cardiovascular tissue sample if it is found to be atherosclerotic.

19. A system for determining if a cardiovascular tissue sample is calcified atherosclerotic, fibrous atherosclerotic, or normal, comprising:

a) means for producing a monochromatic beam of infrared light;

b) means for producing a monochromatic beam of fluorescence inducing light;

c) means for directing said monochromatic beam of infrared light to the cardiovascular tissue sample and for collecting Raman scattered light from the cardiovascular tissue sample;

d) means for directing said monochromatic beam of fluorescence inducing light to the cardiovascular tissue sample and for collecting fluorescent light from the cardiovascular tissue sample;

e) means, coupled to said Raman scattered light collecting means, for producing a Raman spectrum for the cardiovascular tissue sample;

f) means, coupled to said fluorescence collecting means, for producing a fluorescence spectrum for the cardiovascular tissue sample;

g) means for comparing said Raman spectrum for the cardiovascular tissue sample to standard Raman spectra for calcified atherosclerotic tissue and for fibrous atherosclerotic tissue or normal tissue for the same type of tissue being tested; and h) means for comparing said fluorescence spectrum for the cardiovascular tissue sample to standard fluorescence spectra for fibrous atherosclerotic tissue and for calcified atherosclerotic tissue or normal tissue for the same type of tissue being tested.

20. The system as claimed in claim 19 further comprising means for ablating the cardiovascular tissue sample if it is found to be atherosclerotic.

21. A system for determining if a cardiovascular tissue sample is calcified atherosclerotic, fibrous atherosclerotic or normal, comprising:

a) means for producing an imaging light;

b) means for producing a monochromatic beam of infrared light;

c) means for producing a monochromatic beam of fluorescence inducing light;

d) an endoscope comprising in a first channel means for directing said imaging light at the cardiovascular tissue sample and for collecting an image of the cardiovascular tissue sample and in a second channel means for directing said monochromatic beam of infrared light and said monochromatic beam of fluorescence inducing light at the cardiovascular tissue and for collecting the Raman scattered light and the fluorescence from the cardiovascular tissue;

e) means, coupled to said collection means in said first channel, for displaying said image of the cardiovascular tissue sample;

f) means, coupled to said collection means in said second channel, for producing a Raman spectrum for the cardiovascular tissue sample;

g) means for comparing said Raman spectrum for the cardiovascular tissue sample with standard Raman spectra for calcified atherosclerotic tissue and fibrous atherosclerotic tissue or normal tissue for the same type of tissue being tested;

h) means for displaying the results of said Raman comparison;

i) means, coupled to said collection means in said second channel, for producing a fluorescence spectrum for the cardiovascular tissue sample;

j) means for comparing said fluorescence spectrum for the cardiovascular tissue sample with standard fluorescence spectra for fibrous atherosclerotic tissue and calcified atherosclerotic tissue or normal tissue for the same type of tissue being tested; and k) means for displaying the results of said fluorescence comparison.

22. The system as claimed in claim 21 further comprising means for ablating the cardiovascular tissue sample if it is found to be atherosclerotic.

* * * * *